United States Patent [19]

O'Connell et al.

[11] Patent Number: 5,272,084
[45] Date of Patent: Dec. 21, 1993

[54] CELL CULTURE VESSELS HAVING INTERIOR RIDGES AND METHOD FOR CULTIVATING CELLS IN SAME

[75] Inventors: Dennis M. O'Connell, Corning; Martin S. Paris, Big Flats, both of N.Y.

[73] Assignee: Corning Incorporated, Corning, N.Y.

[21] Appl. No.: 809,345

[22] Filed: Dec. 18, 1991

[51] Int. Cl.⁵ .......................... C12N 5/00; C12M 1/22; C12M 3/00

[52] U.S. Cl. .......................... 435/240.243; 435/240.2; 435/284; 435/296; 435/297; 215/DIG. 3

[58] Field of Search .................. 435/284–286, 435/296–299; 220/670, 671, DIG. 13, DIG. 14; 215/DIG. 3; 206/205

[56] References Cited

U.S. PATENT DOCUMENTS

| | | | |
|---|---|---|---|
| D. 285,725 | 9/1986 | Franchere | D24/56 |
| 3,065,150 | 11/1962 | Kravitz | 435/297 |
| 3,097,070 | 11/1958 | Aldrich et al. | 435/297 |
| 3,249,504 | 5/1966 | Cappel et al. | 435/240.3 |
| 3,532,605 | 10/1970 | Riera | 435/296 |
| 3,589,983 | 6/1971 | Holderith et al. | 435/296 |
| 3,632,478 | 1/1972 | Fink | 435/297 |
| 3,701,717 | 10/1972 | Ingvorsen | 435/296 |
| 3,853,712 | 12/1974 | House et al. | 435/284 |
| 3,870,602 | 3/1975 | Froman et al. | 435/284 |
| 3,893,887 | 7/1975 | Smith et al. | 435/240.23 |
| 3,941,661 | 3/1976 | Noteboom | 435/285 |
| 3,948,732 | 4/1976 | Haddad et al. | 435/284 |
| 4,024,975 | 5/1977 | Uhlig | 215/1 C |
| 4,121,976 | 10/1978 | Gleeson | 435/296 |
| 4,157,280 | 6/1979 | Halbert et al. | 435/288 |
| 4,172,013 | 10/1979 | Skoda et al. | 435/285 |
| 4,242,459 | 12/1980 | Chick et al. | 435/283 |
| 4,317,886 | 3/1982 | Johnson et al. | 435/285 |
| 4,333,263 | 6/1982 | Adey | 47/1.4 |
| 4,514,499 | 4/1985 | Noll | 435/284 |
| 4,657,867 | 4/1987 | Guhl et al. | 435/284 |
| 4,665,035 | 5/1987 | Tunac | 435/296 |
| 4,734,373 | 3/1988 | Bartal | 435/296 |
| 4,770,854 | 9/1988 | Lyman | 435/284 |
| 4,789,628 | 12/1988 | Nayak | 435/7 |
| 4,790,361 | 12/1988 | Jones et al. | 215/1 C |
| 4,824,787 | 4/1989 | Serkes et al. | 435/285 |
| 4,829,004 | 4/1989 | Varani et al. | 435/296 |
| 4,912,048 | 3/1990 | Smith et al. | 435/296 |
| 4,912,058 | 3/1990 | Mussi et al. | 435/285 |
| 4,939,151 | 7/1990 | Bracehowski et al. | 435/284 |
| 4,945,061 | 7/1990 | Iskander | 435/298 |
| 4,962,033 | 10/1990 | Serkes et al. | 435/240.243 |
| 5,010,013 | 4/1991 | Serkes et al. | 435/285 |
| 5,017,341 | 5/1991 | Takekawa | 422/102 |
| 5,084,393 | 1/1992 | Rogalsky | 435/284 |
| 5,151,366 | 9/1992 | Serkes et al. | 435/285 |

FOREIGN PATENT DOCUMENTS

| | | |
|---|---|---|
| 0345415 | 12/1989 | European Pat. Off. |
| 1191951 | 10/1959 | France |
| 1413545 | 11/1964 | France |
| WO86/04085 | 7/1986 | PCT Int'l Appl. |
| 9002793 | 3/1990 | World Int. Prop. O. |

OTHER PUBLICATIONS

In Vitro Advertisement.
Medical Polymers And Plasma Technology, *Plasnma Science, Technical Notes*, S. L. Kaplan, T. S. Dunn and P. W. Rose, Belmont, Calif., Oct., 1988, pp. 1–6.
Identifying and Correcting Common Cell Culture Growth and Attachment Problems, J. A Ryan, Cell Culture, Jan. 1989, pp. 8–16.
Surface Treatments and Cell Attachment, W. S. Ramsey, et al., Oct. 1981. In Vitro, vol. 20, No. pp. 802–808.

*Primary Examiner*—Robert J. Warden
*Assistant Examiner*—T. A. Trembley
*Attorney, Agent, or Firm*—Brian R. Leslie

[57] ABSTRACT

The disclosed invention relates generally to laboratory ware, and specifically to laboratory ware and method for cultivating biological cell cultures within the laboratory ware. Cell culture vessels are disclosed providing enhanced cell yields for epithelial-like cell lines, and a more in-vivo like cell growing environment for fibroblast-like cell lines. A representative flask and dish including a plurality of grooves, or valleys, residing between ridges substantially covering the interior of preferably the bottom wall of the flask and dish is disclosed. The preferred ridges have a radius between 0.1 and 0.5 millimeters and range from 0.2 to 2.0 millimeters in height, and are spaced apart from each other within the range of 0.2 to 2.5 millimeters.

16 Claims, 3 Drawing Sheets

CELL CULTURE VESSELS HAVING INTERIOR RIDGES AND METHOD FOR CULTIVATING CELLS IN SAME

BACKGROUND OF THE INVENTION

1. Field of the Invention

The invention relates generally to laboratory ware, and more particularly to vessels, such as flasks and dishes, and methods for cultivating biological cell cultures therein.

2. Description of the Prior Art

The use of vessels for the cultivation of biological cell tissues is well known within the art of growing and propagating cell cultures in-vitro. The cells, and the by-products of the cells cultivated in such vessels, are used in a wide variety of biotechnology related endeavors including pharmacology, genetic research and engineering, and general medical applications.

Prior art vessels generally include a primary growing surface within the vessel which is most often a planar surface in which cells adhere upon while being cultivated. The prior art also includes tissue cell vessels known as roller bottles which are specifically designed to be slowly rotated about the longitudinal axis of the bottle to circulate a medium about the cells anchored upon the interior surface thereof. Such prior art roller bottles may also include as a design feature, corrugated, or pleated, side walls to increase the interior planar surface area in which tissue cells will adhere and grow upon without increasing the overall exterior dimensions of the bottle.

Notwithstanding the prior art, there remains a need in the art for cell culture vessels having improved cell growth, and depending upon the purpose of the culture being cultivated, cell by-product yields. Additionally, there is a need to maintain essentially standardized overall external dimensions of certain capacity vessels in order to be easily accommodated by existing incubators widely used within the art.

OBJECTS OF THE INVENTION

It is an object of this invention to provide cell culture vessels having improved cell growth and possibly cell by-product yields.

It is a further object of this invention to provide improved cell culture vessels having outside geometries and dimensions widely accepted, if not standardized, within the field of the invention.

It is a yet further object of this invention to provide improved cell culture vessels and methods which provide a more in-vivo (in the body) like growing environment for the cell lines likely to be cultivated therein.

These and other objects are achieved by embodiments of the invention described and shown herein.

SUMMARY OF THE INVENTION

A cell culture vessel having at least one side wall and a bottom wall is also disclosed. At least a portion of the interior surface of one of the walls of the vessel is provided with a plurality of grooves, or valleys, configured and sized to be spannable by biological cells thereby emulating in-vivo growing conditions. In a preferred embodiment, the grooves, or valleys, are between ridges that are positioned parallel to each other, or alternatively, concentric with each other. Each ridge has a peak radius within the preferred range of 0.10 to 0.50 millimeters, a preferred peak spacing ranging from 0.2 to 2.5 millimeters from the peak on the adjacent ridge, and a preferred peak height within the range of 0.2 to 2.0 millimeters.

A cell culture flask having a plurality of walls with interior and exterior surfaces, including a top wall and an opposing bottom wall, at least two opposing side walls, and at least two end walls. One of the end walls has an outwardly extending open-ended neck. The interior surface of at least one of the walls has a plurality of grooves, or valleys, configured and sized to be spannable by biological cells. In a preferred embodiment at least a portion of the interior surface of one of the walls of the flask has a plurality of grooves, or valleys, residing between parallel ridges. Each ridge has a peak radius preferably ranging from 0.1 to 0.5 millimeters, a peak spacing preferably ranging from 0.2 to 2.5 millimeters from the peak on the adjacent ridge, and a peak height preferably ranging from 0.2 to 2.0 millimeters.

A method of propagating biological cells in-vitro in an in-vivo like environment is disclosed. The method includes providing a vessel having at least a portion of an interior surface having a plurality of grooves, or valleys, that are spannable by biological cells. Preferably, the grooves, or valleys, are located between ridges that are positioned parallel to each other, or alternatively, concentric with each other. Each ridge has a preferred peak spacing ranging from 0.2 to 2.5 millimeters from the peak on the adjacent ridge, a preferred peak radius ranging from 0.1 to 0.5 millimeters, and a preferred peak height within the range of 0.2 to 2.0 millimeters. The method further includes introducing cells and a growing medium to the vessel wherein the provided ridges allow certain cell lines to span from ridge to ridge thereby emulating an in-vivo like environment.

DETAILED DESCRIPTION OF THE DRAWINGS

Figure 1:
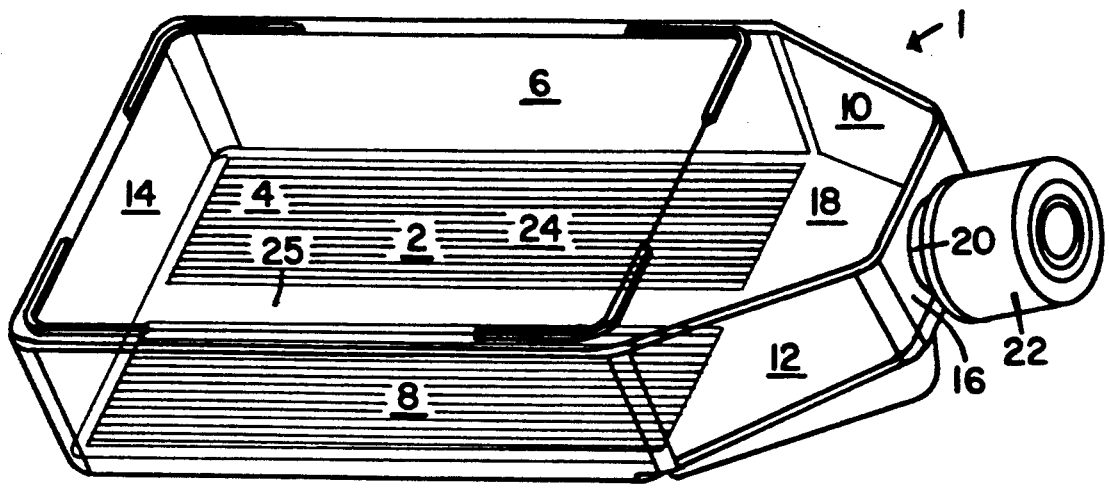
FIG. 1 is a top perspective view of a cell culture flask embodying the disclosed invention.
Figure 2:
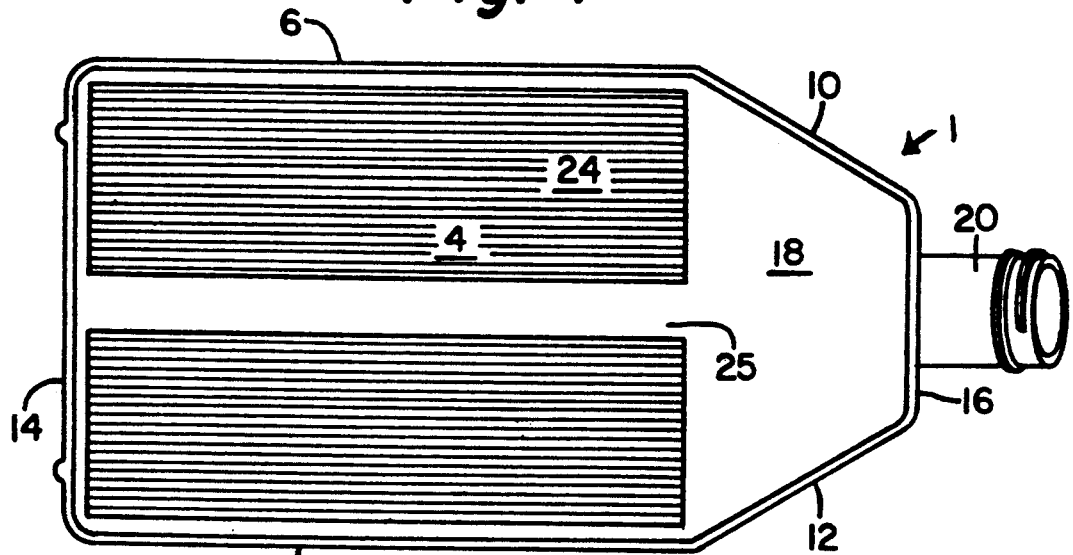
FIG. 2 is a top view of the interior surface of the bottom wall of the culture flask shown in FIG. 1.

Referring now to FIGS. 1 and 2. A cell culture flask 1, having a plurality of walls having interior and exterior surfaces, is shown in perspective. Flask 1 is provided with top wall 2, a bottom wall 4, opposing side walls 6 and 8, and opposing end walls 14 and 16. Flask 1 includes side walls 10 and 12 which extend from side walls 6 and 8 respectively and converge upon and join elevated end wall 16. Ramp surface 18 is inclined with respect to bottom wall 4 and extends laterally between side walls 10 and 12 and upward to end wall 16. End wall 16 has an open-ended neck extending therefrom in order to allow cells and growing medium to be introduced and extracted from the interior of flask 1 by various instruments including pipettes and scraping tools. Removable closure 22 may be removably installed upon open-ended neck 20 in order to seal the interior of flask 1.

The interior surface of bottom wall 4 of flask 1 is provided with a plurality of continuous parallel raised ridges 24 to provide several grooves, or valleys, therebetween. A top view more clearly showing the positioning of continuous parallel ridges 24 upon bottom wall 4 of flask 1 is shown in FIG. 2 of the drawings. The ridges cover substantially all of the available interior surface of bottom wall 4 in order to provide the cells to be cultivated the greatest opportunity to span from a given ridge to an adjacent ridge. The spanning cells are, for the most part, not directly attached to the interior of the vessel but, are instead, attached to each other. Thus, the cells that span across the valley or groove located between adjacent ridges, allow for the circulation of growing medium and the expulsion of by-products between those cells and the interior surface of the vessel thereby more closely emulating cells existing within in-vivo conditions. Such bridging provides a more in-vivo like cell growth, especially with respect to fibroblast-like cells, and thus may enhance cell by-product yields, as compared to conventional growing vessels wherein the cells attach themselves directly to planar or curvilinear interior surfaces.

Fibroblast-like cells refers to cells having elongated fibrous structures which usually grow overlapping each other such as human lung cells MRC5. Fibroblast-like cell lines are distinguishable from epithelial-like cell lines which are identifiable by polar cuboidal cell structure usually growing in a monolayer. An example of an epithelial-like cell line includes cannine kidney cells MDCK.

Figure 3A:
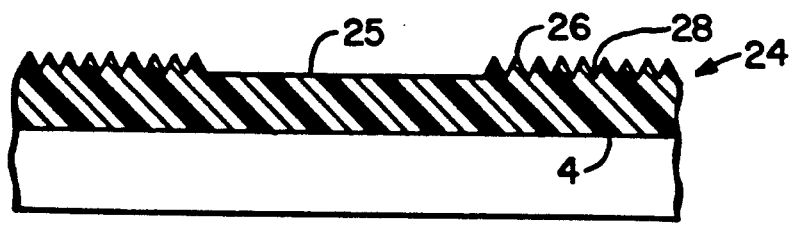
FIG. 3A is a cross-sectional end view of the cell culture flask shown in FIG. 1.
Figure 3B:
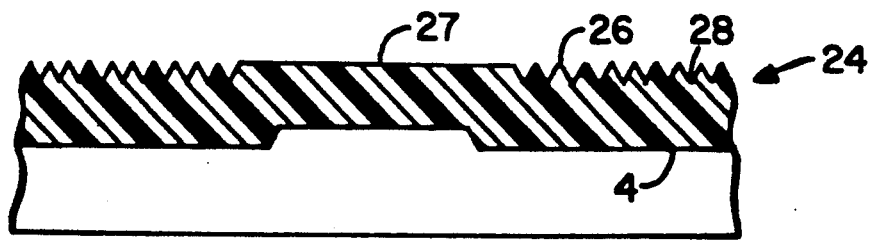
FIG. 3B is a cross-sectional end view of the cell culture flask shown in FIG. 1 provided with an optional elevated planar region.

A cross-sectional end view of preferred ridges 24 is shown in FIG. 3A and FIG. 3B of the drawings. It is preferred that the ridges have an essentially triangular cross-section with peaks 26 being the highest portion of a given ridge, and groove or valley, 28 being the lowest portion between two adjacent ridges.

Notwithstanding the benefit of substantially covering the interior surface of bottom wall 4 with ridges 24 to enhance the likelihood of cell bridging, it may be desirable to have at least one portion of the surface not covered with ridges, or grooves or valleys, in order to more conveniently view cells microscopically in situ on a planar surface. Thus flask 1, as illustrated in FIGS. 1 through 3A, has a planar area 25, and FIG. 3B illustrates an elevated planar viewing area 27 for microscopically viewing cells being cultured within the flask. Planar area 25, as shown in FIG. 3A, is positioned at a height below the peaks 26 of ridges 24. Elevated planar area 27, as shown in FIG. 3B, is positioned at essentially the same height as peaks 26 of ridges 24 to facilitate the removal of cells from elevated planar area 27 by cell scraper tools that are commonly inserted through neck 20 and brought into contact with surfaces upon which cells are growing. Thus, a cell scraper of a given width, will not merely contact the peaks of the ridges, or the highest most portion of the interior surface, the scraper will instead contact the planar region without special effort on part of a lab technician.

It is also preferred that ridges 24 extend longitudinally along the major axis of the vessel, as shown in FIGS. 1 and 2, which is typically in line with outwardly extending neck 20. By positioning the ridges longitudinally, the removal of cultured cells from the faces of the ridges when using a cell scraper tool that has been inserted through neck 20 is expedited. By such positioning, the tool need not traverse the ridges in a cross-wise manner, but may simply be raked along the ridges.

Figure 4:
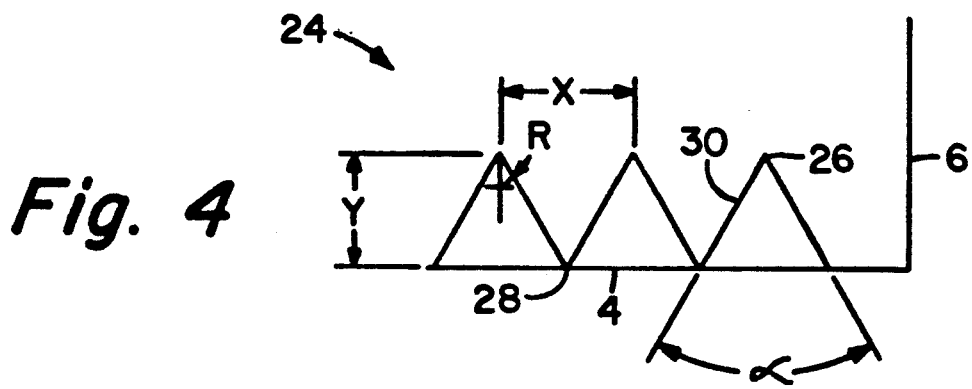
FIG. 4 is an enlarged isolated cross-sectional end view of the cell culture flask shown in FIG. 1.

An enlarged isolated cross-sectional view more precisely showing ridges 24 located on bottom wall 4 is shown in FIG. 4. Ridge peaks 26 are spaced apart from each other by dimension X that preferably ranges from 1.0 to 2.5 millimeters. Height of peaks 26 from the interior surface of bottom wall 4 is shown as dimension Y. Dimension Y preferably ranges from 0.2 to 2.0 millimeters. Radius of peaks 26, shown as dimension R, preferably ranges from 0.1 to 0.5 millimeters. Angle $\alpha$ is the angle between sloped facings 30 that form a single ridge 24. Angle $\alpha$ is approximately 40° for the preferred ridge profiles. Table 1 provides dimensional data for dimensions X, Y, R, and $\alpha$ as depicted in FIG. 4, of three example ridge profiles.

TABLE 1

| Dimension: (millimeters) | X | Y | R | $\alpha$ |
|---|---|---|---|---|
| Example Ridge Profile 1 | 2.08 | 1.52 | 0.36 | 39°50'23" |
| Example Ridge Profile 2 | 1.17 | 0.66 | 0.13 | 39°50'29" |
| Example Ridge Profile 3 | 0.76 | 0.66 | 0.13 | 39°50'37" |

It was found that, of the three examples, Example Ridge Profile 3 required the least amount of saline solution to rinse the cell interior growing surfaces of medium. Example Ridge Profile 3 also required the least amount of enzyme to dissociate cells from the growing surfaces.

Figure 5:
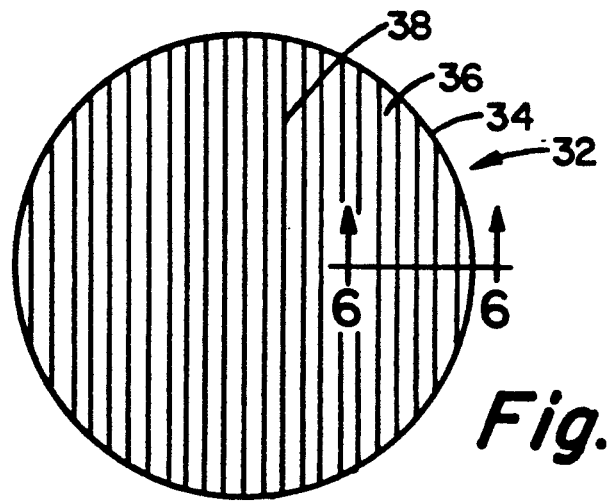
FIG. 5 is a top view of a cell culture dish embodying the disclosed invention.
Figure 6:
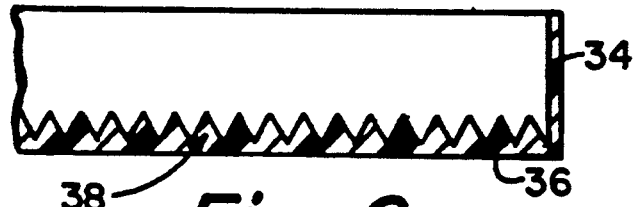
FIG. 6 is a cross-sectional side view of the cell culture dish shown in FIG. 5.

A top view of a cell culture vessel incorporating the preferred ridge profile is shown in FIG. 5. Dish 32 includes an annular side wall 34 and a bottom wall 36. The interior surface of bottom wall 36 is essentially covered with a plurality of parallel ridges 38. FIG. 6 is an enlarged isolated cross-sectional view taken along the line 6—6 of FIG. 5 to more clearly show ridges 38.

Figure 7:
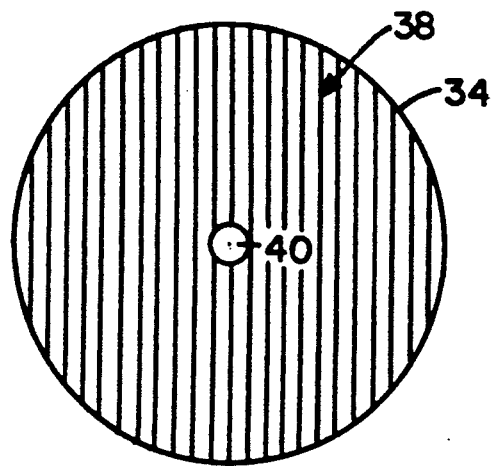
FIG. 7 is a top view of a cell culture dish with an alternative planar region or viewing area.

If so desired, a portion of bottom wall 36 may remain free of grooves, or valleys, in order to provide a planar area, or window 40, for the microscopic viewing of cells in situ. Such a window 40 is included in the top view of the vessel shown in FIG. 7 of the drawings. Window 40 need not be of any particular geometry as the purpose of window 40 is to provide a horizontal area where representative cells of the culture may be easily viewed through a microscope. The viewing area may also be positioned at the same height as the peaks of the ridges in order to facilitate the scraping of cells from the viewing area by cell scraping tools or other instruments.

Figure 8:
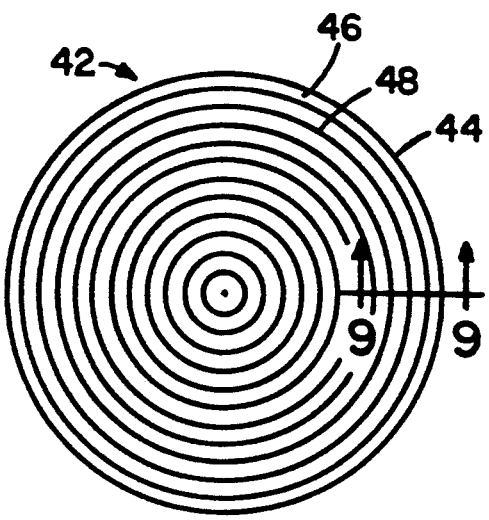
FIG. 8 is a top view of a cell culture dish incorporating an alternative embodiment of the disclosed invention.
Figure 9:
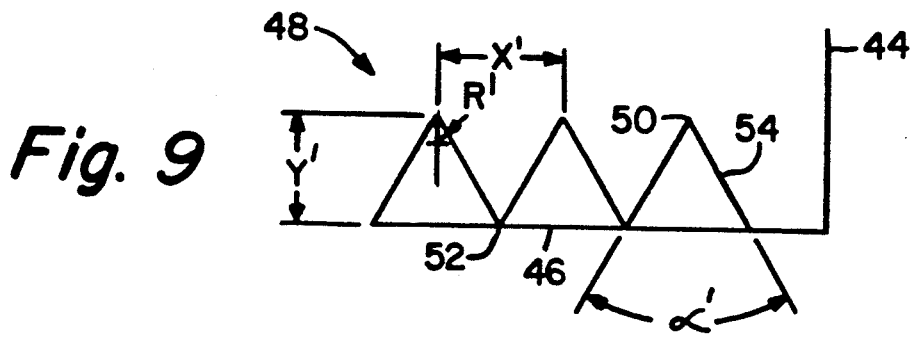
FIG. 9 is an enlarged isolated cross-sectional end view of the cell culture dish shown in FIG. 8.

A top view of an exemplary cell culture dish provided with an alternative embodiment of the invention is shown in FIG. 8. Cell culture dish 42 has an annular side wall 44 and a bottom wall 46. The interior surface of bottom wall 46 has a plurality of concentric ridges 48 which decrease in diameter as a function of the distance from the center of bottom wall 46. FIG. 9 is an enlarged isolated cross-sectional view of dish 42 taken along sectional line 9—9 shown in FIG. 8. Peaks 50 having a radius R' preferably between 0.1 and 0.5 millimeters are separated by grooves or valleys 52 with adjacent peaks 50 being spaced apart from each other by a distance shown as dimension X'. Dimension X' preferably ranges between 0.2 and 2.0 millimeters. Approximately 1.2 millimeters has been found to be suitable for X' for a wide range of cell lines likely to be cultured within dish 42. The height of peaks 50 from the interior surface of bottom wall 46 is shown as dimension Y'. Dimension Y' preferably ranges from 0.2 to 2.0 millimeters, with approximately 0.9 millimeters being optimum for a wide range of cell lines likely to be cultured within the disclosed vessel. Angle $\alpha'$ is the angle between sloped facings 54 that form a single ridge 50. Angle $\alpha'$ typically approximates 40° with 39°50'29" being particularly suitable for a variety of cell lines.

Figure 10:
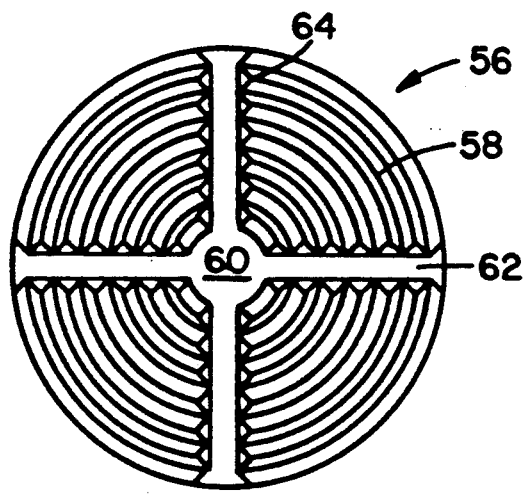
FIG. 10 is a top view of a cell culture dish incorporating an alternative embodiment of the disclosed invention.

A representative cell culture dish having alternatively preferred concentric ridges and additionally having drainage and viewing areas is shown in FIG. 10 of the drawings. Cell culture dish 56 is much the same as previously described cell culture dish 42 with the exception that concentric ridges 58 are centrally located about a planar, or window area 60. Culture dish 56 also has a plurality of non-ridge regions 62 extending outwardly therefrom. Window 60 and regions 62 may be positioned at an elevation which is lower than peaks 64 of ridges 58 in order to provide a drainage region to accommodate surplus growing medium, or window 60 and regions 62 may be positioned at an elevation which is at least as high as peaks 64 ridges 58, with respect to the interior surface, in order to provide an elevated viewing area in which cells will be able to be more easily viewed through a microscope and/or removed by a cell scraping tool. The window/channel configuration shown in FIG. 10 is merely representational, as various combinations, configurations and spacings can be utilized.

Although it is preferred to utilize ridges having certain configurations described herein, it can be appreciated that configurations other than generally triangular-shaped ridges may be employed to provide a valley, or groove, in which certain cell lines may span across while simultaneously providing surface areas in which cells may adhere. For example, ridges having truncated, or more rounded peaks in lieu of relatively sharp peaks may be used. Rectangular, or rounded grooves, or valleys, serve as examples of various configurations that may be employed in lieu of the preferred triangular-shaped groove and ridge profile. However, alternatively configured grooves, or valleys, preferably have a nominal width that are spannable by cells thereby providing a more in-vivo like environment for cell growing purposes.

Vessels embodying the invention may be formed of any material suitable for cell culture laboratory ware known within the art, including a wide variety of biocompatible plastics that are surface treatable and sterilizable. Injection-moldable styrene-based plastics have been found to be particularly suitable for forming such vessels.

Although preferred embodiments of the disclosed invention have been described and shown herein, it will be apparent to those skilled in the art, that aspects of the disclosed invention may be modified without departing from the spirit and scope of the invention as claimed.

We claim:

1. A cell culture flask comprising: a plurality of walls having interior and exterior surfaces, said plurality of walls including a top wall and an opposing bottom wall, at least two opposing side walls, and at least two end walls, one of the end walls having an outwardly extending open-ended neck; and a portion of at least one of the interior surfaces of one of the walls having an area containing a plurality of alternating ridges and grooves, or valleys, the plurality of ridges being configured and the plurality of grooves being sized to be spanable by fibroblast-like tissue culture cells such that said fibroblast-like tissue culture cells form bridges between ridges of said plurality of ridges which allow for circulation of growing medium between said fibroblast-like tissue culture cells and the interior surface of the flask.

2. The cell culture flask of claim 1 wherein the area containing the plurality of alternating ridges and grooves, or valleys, covers a majority of the interior surface of the bottom wall.

3. The cell culture flask of claim 1 wherein the flask has a major axis and a minor axis and wherein the plurality of alternating ridges and grooves, or valleys, are parallel to the major axis, each ridge of said plurality of ridges has a peak which has a radius between 0.1 and 0.5 millimeters, each peak is spaced from the peak on an adjacent ridge within a range of 0.2 to 2.5 millimeters, and each ridge has a peak height ranging from 0.2 to 2.0 millimeters.

4. The cell culture flask of claim 1 wherein a portion of the bottom wall is inclined to form a ramp proximate to the end wall having said outwardly extending open-ended neck.

5. The cell culture flask of claim 1 wherein the interior surface of the bottom wall has a planar window area.

6. The cell culture flask of claim 1 wherein the area containing the plurality of alternating ridges and grooves, or valleys, covers a portion of the interior surface of the bottom wall, each ridge of said plurality of ridges having a specified peak height, and the flask further comprises an elevated planar area positioned on the interior surface of the bottom wall, said elevated planar area having at least the same height as the specified peak height of each of said plurality of ridges.

7. An improved cell culture flask having a major axis and a minor axis and having a plurality of flask walls having an interior surface and an exterior surface, the plurality of flask walls including a top wall and an opposing bottom wall in which a portion thereof forms an inclined ramp, at least two end walls, one of the end walls being proximate to the inclined ramp and further having an outwardly extending open-ended neck formed to accept a removable closure wherein the improvement comprises: an area covering a majority of the interior surface of the bottom wall, the area having a plurality of continuous parallel ridges, the plurality of continuous parallel ridges extending parallel to the major axis of the flask, each ridge of said plurality of ridges having a peak with a radius between 0.1 to 0.5 millimeters, the peak on each ridge being spaced from the peak on an adjacent ridge within a range of 0.2 to 2.5 millimeters, and each ridge having a peak height ranging from 0.2 to 2.0 millimeters whereby fibroblast-like tissue culture cells can span between the ridges of said plurality of ridges to form bridges which allow for circulation of growing medium between said fibroblast-like tissue culture cells and the interior surface of the bottom wall.

8. An improved cell culture vessel having at least one side wall and a bottom wall, each wall having an interior surface and an exterior surface, wherein the improvement comprises: at least a portion of the interior surface of side wall or said at least one said bottom wall has a plurality of alternating ridges and grooves, or valleys, the plurality of ridges being configured and the plurality of grooves being sized to be spanable by fibroblast-like tissue culture cells such that said fibroblast-like tissue culture cells form bridges between ridges of said plurality of ridges which allow for circulation of growing medium between said fibroblast-like tissue culture cells and the interior surface of the vessel.

9. The cell culture vessel of claim 8 wherein said at least one side wall is annular thereby forming a circular dish, and the plurality of alternating ridges and grooves, or valleys, are parallel to each other.

10. The cell culture vessel of claim 8 wherein the plurality of alternating ridges and grooves, or valleys, are parallel to each other.

11. The cell culture vessel of claim 8 wherein the plurality of alternating ridges and grooves, or valleys, are concentric to each other.

12. The cell culture vessel of claim 8 wherein each ridge of said plurality of ridges has a peak which has a radius between 0.1 and 0.5 millimeters, each peak is spaced from 0.2 to 2.5 millimeters from the peak on an adjacent ridge, and each ridge has a peak height of 0.2 to 2.0 millimeters.

13. The cell culture vessel of claim 8 wherein the interior surface of the bottom wall further comprises at least one planar window area.

14. The cell culture vessel of claim 8 wherein at least a portion of the interior surface of the bottom wall has the plurality of alternating ridges and grooves, or valleys, each ridge having a specified peak height, and the cell culture vessel further comprises an elevated planar window area positioned on the interior surface of the bottom wall, said elevated planar window area having at least the same height as the specified peak height of each of the ridges of said plurality of ridges.

15. A method of growing biological cell lines in an in-vivo like environment comprising:
 a) providing a vessel having at least one side wall and a bottom wall, each wall having an interior surface, at least one of the interior surfaces having a plurality of alternating ridges and grooves, or valleys, the plurality of ridges being configured and the plurality of grooves being sized to be spanable by fibroblast-like tissue culture cells such that said fibroblast-like tissue culture cells form bridges between ridges which allow circulation of growing medium between said fibroblast-like tissue culture cells and the interior surface of the vessel;
 b) introducing a growing medium to the vessel; and
 c) introducing at least one selected cell line to the vessel wherein a portion of the cells ultimately span across at least some of the plurality of grooves, or valleys.

16. The method of claim 15 wherein each ridge of said plurality of ridges has a peak which has a radius between 0.1 and 0.5 millimeters, each peak is spaced from 0.2 to 2.5 millimeters from the peak on an adjacent ridge and each ridge has a peak height of 0.2 to 2.0 millimeters.

* * * * *